US 11,702,689 B2

(12) United States Patent
Chen et al.

(10) Patent No.: US 11,702,689 B2
(45) Date of Patent: Jul. 18, 2023

(54) HOMOPOLYMER PRIMERS FOR AMPLIFICATION OF POLYNUCLEOTIDES CREATED BY ENZYMATIC SYNTHESIS

(71) Applicant: MICROSOFT TECHNOLOGY LICENSING, LLC, Redmond, WA (US)

(72) Inventors: Yuan-Jyue Chen, Seattle, WA (US); Bichlien Nguyen, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 525 days.

(21) Appl. No.: 16/858,253

(22) Filed: Apr. 24, 2020

(65) Prior Publication Data
US 2021/0332412 A1 Oct. 28, 2021

(51) Int. Cl.
*C12Q 1/68* (2018.01)
*C12Q 1/686* (2018.01)
(Continued)

(52) U.S. Cl.
CPC .......... *C12Q 1/686* (2013.01); *G16B 30/00* (2019.02); *G16B 40/00* (2019.02);
(Continued)

(58) Field of Classification Search
CPC ..................................................... C12Q 1/68
(Continued)

(56) References Cited

U.S. PATENT DOCUMENTS

| 2002/0107372 A1* | 8/2002 | Hefeneider | C07K 14/705 |
| | | | 536/23.1 |
| 2003/0180802 A1* | 9/2003 | Kloek | C12N 15/8247 |
| | | | 435/7.1 |
| 2007/0009981 A1* | 1/2007 | Williams | C12N 9/1007 |
| | | | 435/468 |
| 2012/0283106 A1* | 11/2012 | Wang | C12Q 1/6851 |
| | | | 435/6.12 |

(Continued)

FOREIGN PATENT DOCUMENTS

| EP | 3067809 A1 * | 9/2016 |
| EP | 3506135 A1 | 7/2019 |

(Continued)

OTHER PUBLICATIONS

"International Search Report and Written Opinion Issued in PCT Application No. PCT/US2021/022453", dated Jun. 17, 2021, 10 Pages.

*Primary Examiner* — Aaron A Priest
(74) *Attorney, Agent, or Firm* — Benjamin Keim; Newport IP, LLC

(57) ABSTRACT

This disclosure describes a technique for performing random access in a pool of polynucleotides by using one unique primer and one homopolymer primer to selectively amplify some but not all of the polynucleotides in the pool. The polynucleotides are synthesized by a template independent polymerase such as terminal deoxynucleotide transferase (TdT) rather than by phosphoramidite synthesis. Enzymatic synthesis efficiently creates homopolymer sequences through unregulated synthesis. Use of one homopolymer primer instead of two unique primers decreases the complexity, time, and cost of synthesizing the polynucleotides. Use of a unique primer provides a sequence that can be varied to uniquely identify multiple different groups of polynucleotides. This enables random access by polymerase chain reaction (PCR) amplification while still benefitting from the efficiency of homopolymer synthesis. The poly- (Continued)

nucleotides may include payload regions that use a sequence of nucleotides to encode digital data.

20 Claims, 6 Drawing Sheets

(51) Int. Cl.
  *G16B 30/00* (2019.01)
  *G16B 40/00* (2019.01)
(52) U.S. Cl.
  CPC .... *Y10S 707/964* (2013.01); *Y10S 707/99931* (2013.01); *Y10S 707/99941* (2013.01)
(58) Field of Classification Search
  USPC ......................................................... 435/6.1
  See application file for complete search history.

(56) References Cited

U.S. PATENT DOCUMENTS

| 2017/0141793 A1* | 5/2017 | Strauss | ................ H03M 13/611 |
| 2019/0345488 A1* | 11/2019 | Soumillon | ........... C12Q 1/6806 |
| 2022/0195515 A1* | 6/2022 | Van Oudenaarden | ....................... C12Q 1/6874 |

FOREIGN PATENT DOCUMENTS

| WO | 2004081225 A2 | 9/2004 | |
| WO | WO-2007001962 A2 * | 1/2007 | ............... C07K 1/00 |
| WO | WO-2013178801 A2 * | 12/2013 | ............. B82Y 10/00 |
| WO | WO-2016059610 A1 * | 4/2016 | ....... G06F 17/30082 |
| WO | WO-2016164779 A1 * | 10/2016 | ............. G06F 16/00 |
| WO | 2017189914 A1 | 11/2017 | |

* cited by examiner

HOMOPOLYMER PRIMERS FOR AMPLIFICATION OF POLYNUCLEOTIDES CREATED BY ENZYMATIC SYNTHESIS

BACKGROUND

Much of the data being produced by computing devices is stored on conventional data storage systems that include various kinds of magnetic storage media, optical storage media, and/or solid-state storage media. The capacity of conventional data storage systems is not keeping pace with the rates of data being produced by computing devices. Polynucleotides, such as deoxyribonucleic acid (DNA) or ribonucleic acid (RNA), can be used to store very large amounts of data on a scale that exceeds the capacity of conventional storage systems. An arrangement of nucleotides included in a polynucleotide (e.g., CTGAAGT . . . ) can correspond to an arrangement of bits that encodes digital data (e.g., 11010001 . . . ). The digital data can include audio data, video data, image data, text data, software, combinations thereof, and the like.

The retrieval of digital data stored in polynucleotides can be achieved using processes that amplify polynucleotides which encode the digital data that is requested. For example, polymerase chain reaction (PCR) can be used to amplify the polynucleotides that encode digital data. Amplification of polynucleotides produces an amplification product that includes an amount of the polynucleotides being amplified that is several orders of magnitude greater than the original quantity of the polynucleotides.

The amplification of polynucleotides that encode digital data may be performed selectively such that the polynucleotides encoding the desired digital data are amplified while other polynucleotides are not amplified. To illustrate, polynucleotides of two different data files can be stored in a container of a polynucleotide data storage system and one of the data files can be the subject of a request for digital data. This type of selective request for data from a data store is a random access request.

After selective amplification, the number of polynucleotides associated with the requested data file will be orders of magnitude greater than the number of polynucleotides of the other data file. A sample of the amplification product can be sequenced by a polynucleotide sequencer and the sequence data can be decoded to reproduce the original bits of the requested digital data. Although some polynucleotides associated with the data file that was not requested are still provided to the polynucleotide sequencer, the probability of generating sequence data from these polynucleotides is very small because there are many more copies of the polynucleotides encoding the requested data file. Thus, the sequencing data produced by the polynucleotide sequencer corresponds to the requested digital data because the polynucleotides encoding this digital data were selectively amplified before sequencing while the polynucleotides corresponding to the other data file were not.

There are multiple techniques for synthesizing polynucleotides that encode digital data such as the traditional phosphoramidite synthesis and the newer technique of enzymatic synthesis. Techniques for phosphoramidite synthesis are well known to those of ordinary skill in the art. Enzymatic synthesis uses an enzyme, a template independent polymerase, rather than chemical reactions to synthesize polynucleotides. Template independent polymerases are DNA or RNA polymerases that perform de novo polynucleotide synthesis without use of a template strand. One characteristic of template independent polymerases such as TdT is their ability to perform unregulated synthesis by adding any available nucleotide. Synthesis of specific, arbitrary sequences with a template independent polymerase can be achieved by regulating the reaction environment in ways that limit the polymerase to adding one single, specific nucleotide at a time.

SUMMARY

PCR is used as a technique to achieve random access of selected polynucleotides from a pool of multiple different polynucleotides by selectively amplifying the desired polynucleotides. A pair of primers is used to specify which polynucleotides are amplified. The primers hybridize to only those polynucleotides with complementary primer binding sites. The uniqueness of the primers makes it possible to amplify one group of polynucleotides from the pool without amplifying other groups of polynucleotides. Following selective amplification, the sample is sequenced and the increased copy number of the amplified polynucleotides results in the polynucleotide sequencer reading only the amplified polynucleotides. The polynucleotides may encode digital data in a payload sequence and include primer binding sites. All polynucleotides with the same primer binding sites amplify together.

In one illustrative implementation, different primer binding sites correspond to different digital files. Thus, a specific digital file can be selectively retrieved from polynucleotide storage by amplification with primers that correspond to the primer binding sites in the polynucleotides that encode the digital file.

Homopolymer sequences, runs of the same nucleotide, can function as primers for PCR. But homopolymer sequences have only limited ability to uniquely identify a polynucleotide (i.e., there are only four options if using standard nucleotides). Enzymatic synthesis of polynucleotides is, unlike phosphoramidite synthesis, able to readily generate homopolymer sequences by repeatedly adding the same nucleotide. This is because template independent polymerases can perform unregulated synthesis. Unregulated synthesis in a reaction mixture that provides only a single species of nucleotide produces a homopolymer. Homopolymer sequences are easier to create with enzymatic synthesis than specific sequences of varied nucleotides. Generating a homopolymer sequence with enzymatic synthesis uses less time and reagents than generating a specific, varied sequence of the same length.

Pairing a unique primer with a homopolymer primer allows specific polynucleotides to be selectively amplified based on the sequence of nucleotides in the unique primer and benefits from the ease of creating homopolymer sequences with enzymatic synthesis. Thus, synthesizing polynucleotides in which one of the primers is a homopolymer saves, time, reagents, and cost without losing the ability to uniquely identify many different groups of polynucleotides.

Use of a homopolymer primer reduces the total number of unique primer sequences available to distinguish polynucleotides as compared to use of two unique primers. With a pair of unique primers, variations in each primer can distinguish polynucleotides. With one homopolymer primer, most or all of the variation is provided by the single unique primer. In some implementations, an overhang primer can add a unique nucleotide sequence to the end of the homopolymer portion of a polynucleotide. An overhang primer includes a homopolymer region and a unique nucleotide sequence. PCR amplification with an overhang primer creates polynucleotides that include the unique nucleotide sequence appended to the end of the homopolymer sequence. Once added, the unique nucleotide sequence can be used as a second unique primer binding site that together with the first unique primer binding site provides an increased number of unique primer variations for random access.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
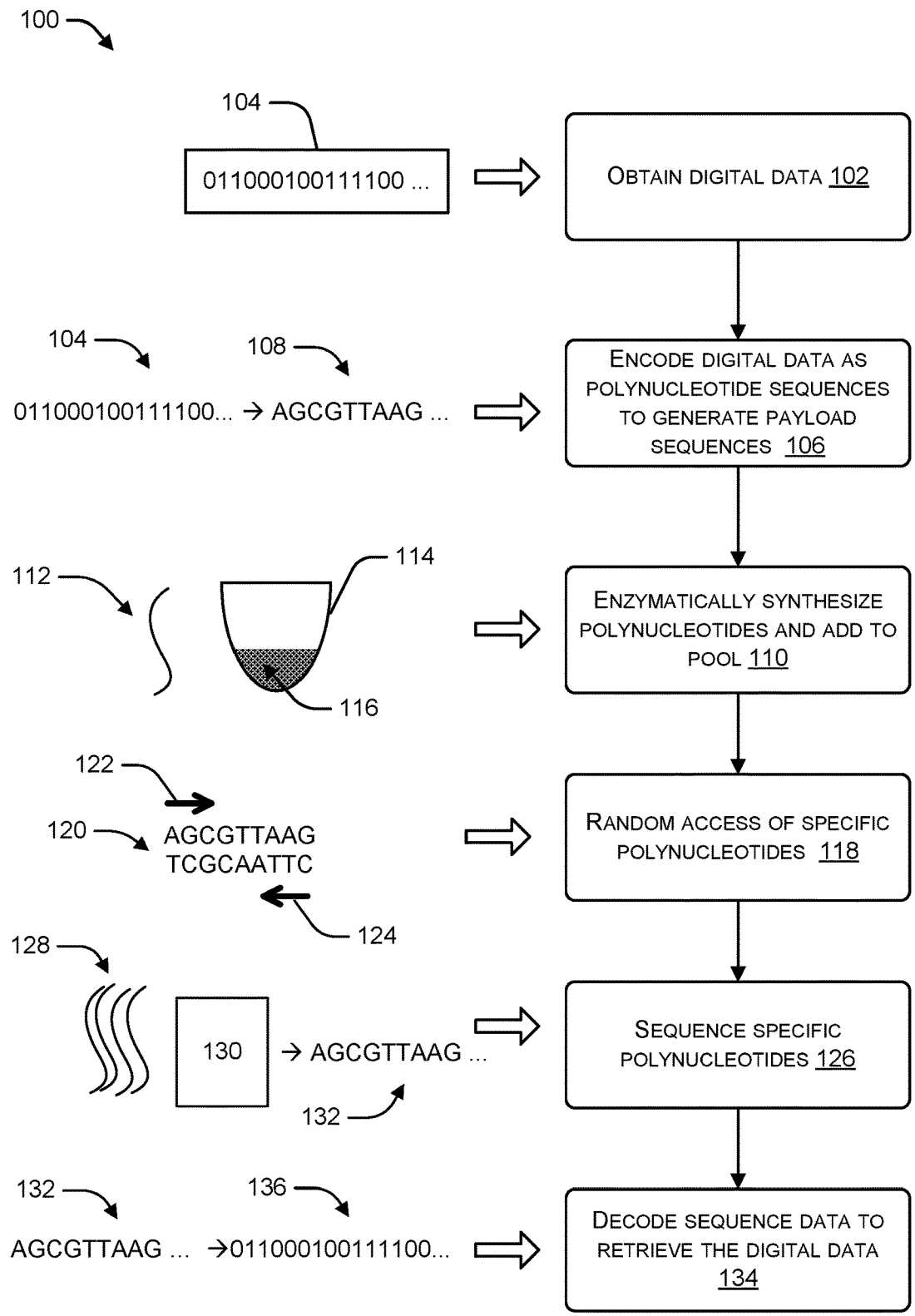
FIG. 1 is a schematic diagram of a process that uses random access to selectively retrieve polynucleotides from a polynucleotide data storage system.

This disclosure describes techniques for using a combination of homopolymer primers and unique primers to perform random access on polynucleotides in a polynucleotide data storage system. Polynucleotide data storage systems use polynucleotides such as DNA to store digital data. The region of a polynucleotide that encodes digital data is referred to herein as a "payload." A nucleotide string encoding the digital data of a single data file may be split into a large number of payload segments. In some implementations, each payload segment is about 100-200 nucleotides long. A pool of polynucleotides or simply "pool" contains multiple polynucleotides each with its respective payload segment. There may be payload segments encoding digital data from multiple different data files in a single pool.

Advantages of using polynucleotides rather than other storage media for storing digital data include information density and longevity. The sequence of nucleotide bases is designed on a computer and then polynucleotides with that sequence are synthesized. The polynucleotides may be stored, selectively retrieved from storage, read by a polynucleotide sequencer, and then decoded to retrieve the digital data.

Proof of concept systems and techniques for storing data in polynucleotides have been previously demonstrated. See Lee Organick et al., *Random Access in Large-Scale DNA Data Storage*, 36:3 Nat. Biotech. 243 (2018) and Christopher N. Takahashi et al., *Demonstration of End-to-End Automation of DNA Data Storage*, 9 Sci. Rep. 4998 (2019). As polynucleotide data storage systems increase in size and complexity the ability to perform random-access requests will become increasingly important. Illustrative techniques for performing random-access using selective PCR amplification are described in Organick, supra and U.S. Pat. App. Publication No. 2018/0265921 entitled "Random Access of Data Encoded by Polynucleotides" filed on Mar. 15, 2017.

In this disclosure, polynucleotides, which are also referred to as oligonucleotides, include both DNA, RNA, and hybrids containing mixtures of DNA and RNA. DNA includes nucleotides with one of the four natural bases cytosine (C), guanine (G), adenine (A), or thymine (T) as well as unnatural bases, noncanonical bases, and/or modified bases. RNA includes nucleotides with one of the four natural bases cytosine, guanine, adenine, or uracil (U) as well as unnatural bases, noncanonical bases, and/or modified bases. Nucleotides include both deoxyribonucleotides and ribonucleotides covalently linked to one or more phosphate groups. The term "polynucleotide sequence" refers to the alphabetical representation of a polynucleotide molecule. The alphabetical representation may be input and stored the memory of a computing device.

Detail of procedures and techniques not explicitly described in this or other processes disclosed of this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, 4$^{th}$ ed. (2012).

Polymerase Chain Reaction

PCR is one molecular biology technique discussed in this disclosure. PCR refers to a reaction for the in vitro amplification of specific DNA sequences by the simultaneous primer extension of complementary strands of DNA. In other words, PCR is a reaction for making multiple copies or replicates of a target nucleic acid flanked by primer binding sites. The reaction comprising one or more repetitions of the following steps: (i) denaturing the target nucleic acid, (ii) annealing primers to the primer binding sites, and (iii) extending the primers by a template-dependent polymerase in the presence of nucleoside triphosphates. Usually, the reaction is cycled through different temperatures optimized for each step in a thermocycler. A thermocycler (also known as a thermal cycler, PCR machine, or DNA amplifier) can be implemented with a thermal block that has holes where tubes holding an amplification reaction mixture can be inserted. Other implementations can use a microfluidic chip in which the amplification reaction mixture moves via a channel through hot and cold zones.

Each cycle doubles the number of copies of the specific DNA sequence being amplified. This results in an exponential increase in copy number. Particular temperatures, durations at each step, and rates of change between steps depend on many factors well-known to those of ordinary skill in the art, e.g., exemplified by the references: McPherson et al., editors, *PCR: A Practical Approach and PCR 2: A Practical Approach* (IRL Press, Oxford, 1991 and 1995, respectively). Illustrative methods for detecting a PCR product using an oligonucleotide probe capable of hybridizing with the target sequence or amplicon are described in Mullis, U.S. Pat. Nos. 4,683,195 and 4,683,202; EP No. 237,362.

A PCR reaction has three main components: a template, primers, and a PCR reaction mixture or "master mix." The template is a single- or double-stranded polynucleotide containing the (sub)sequence of nucleotides to be amplified. The primers are short synthetic oligonucleotides that define the beginning and end of the region to be amplified. Primers are typically between 10-30 nucleotides, 15-25 nucleotides, or 18-22 nucleotides long. The PCR reaction mixture includes one or more template-dependent polymerases, nucleotide triphosphates, a buffer solution, and any cofactors used by the polymerases such as $MgCl_2$. Natural nucleotide triphosphates can include dATP, dCTP, dGTP, dTTP, and dUTP. Nucleoside triphosphates of non-standard nucleotides can also be added if desired or needed.

Template-dependent polymerases are DNA or RNA polymerases that use a single-strand of a polynucleotide as a template to guide the addition of nucleotides in a complementary strand. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Klenow fragment of DNA polymerase I, the HIV-1 polymerase, and KAPA HIFI polymerase available from Kapa Biosystems.

In one illustrative protocol, a 20 µL PCR reaction, 1 µL of 1 ng/µL of ssDNA pool is mixed 1 µL of 10 uM of s forward primer (e.g., a unique primer) and 1 µL of 10 uM of a reverse primer (e.g., a homopolymer primer), 10 µL of 2× KAPA HIFI enzyme mix, and 7 µL of molecular biograde water. The reaction uses a thermal protocol: (1) 95° C. for 3 min, (2) 98° C. for 20 sec, (3) 62° C. for 20 sec, (4) 72° C. for 15 sec.

Primers are complementary to and hybridize with primer binding sites. By "hybridizable" or "complementary" or "substantially complementary" it is meant that a polynucleotide comprises a sequence of nucleotides that enables it to non-covalently bind, to another polynucleotide in a sequence-specific, antiparallel, manner (i.e., a polynucleotide specifically binds to a complementary polynucleotide) under the appropriate conditions of temperature and solution ionic strength.

Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., Molecular Cloning: *A Laboratory Manual, Third Edition*, Cold Spring Harbor Laboratory Press, Cold Spring Harbor (2001). The conditions of temperature and ionic strength determine the "stringency" of the hybridization.

It is understood in the art that the sequence of polynucleotide need not be 100% complementary to that of its target polynucleotide to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target polynucleotide to which they are targeted. For example, an antisense polynucleotide in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. Percent complementarity between particular stretches of polynucleotide sequences within polynucleotides can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Random Access

Random access is the ability to selectively access specific data randomly rather than sequentially. In contrast, sequential access of data requires accessing data in the order it is stored which may result in accessing additional data before accessing the desired data. The ability to selectively access specific data randomly rather than sequentially is a desirable feature in a data storage system.

Without random access on a molecular level, every polynucleotide in a pool of polynucleotides must be sequenced to read data from any of the polynucleotides. The desired data is then obtained by using conventional digital computer techniques to analyze and decode the sequence data. For small pools this may be possible. However, as the scale of polynucleotide data storage systems increases, sequencing the entire pool of polynucleotides for every data request quickly becomes unworkable.

PCR may be used to perform random access of selected polynucleotides from a pool of polynucleotides. Random access in the context of polynucleotide data storage systems allows the requested polynucleotides to be sequenced and decoded without needing to sequence and decode all the polynucleotides in the pool. With this technique, the polynucleotides in the pool have payload regions that encode digital data and the payload regions are flanked by primer binding sites. The pool as a whole may be designed with a correspondence between the primer binding sites and encoded data. For example, all payload sequences encoding data from the same data file may be flanked by the same primer binding sites.

When PCR is performed with a pair of primers that only hybridize to the primer bindings sites of the selected polynucleotides, only the selected polynucleotides are amplified. Thus, the quantity of the selected polynucleotides will be much greater than the other polynucleotides stored with the selected polynucleotides. In this way, the probability of sequencing the selected polynucleotides will be greater than the probability of sequencing the non-target polynucleotides and the sequence data generated by a polynucleotide sequencer can be decoded to reproduce the requested digital data.

Address Space

Address space is the number of unique addresses that can be independently accessed in a storage system that provides for random access. When PCR is used to implement random access, primer specificity determines the number of polynucleotide groups that can be separately amplified and the address space. This type of address space is primarily determined primer length. Primer length can include the length of both forward and reverse primers if both are used to differentiate polynucleotides. The maximum theoretical address space given a four-letter alphabet (i.e., A, G, C, T) is $4^n$ where n is the length of the primers. If two 15-nucleotide long primers are used for selective amplification, then the theoretical maximum address space is $4^{30}$ or $1.15 \times 10^{18}$. If one primer of a primer pair is not used to distinguish between nucleotides (e.g., the reverse is primer is the same for all nucleotides in a pool) then the maximum theoretical address space for a single 15-nucleotide primer is $4^{15}$ or $1.07 \times 10^9$.

However, the actual address space is much lower than the theoretical maximum because many potential primer sequences cannot effectively function as primers for various reasons. Some sequences may be unsuitable as primers because they form secondary structures such as primer-dimers, include long homopolymer sequences, have annealing temperatures that are too high or too low, or anneal to regions of a payload sequence in additional to a primer binding site. One illustrative set of criteria for identifying suitable primers are described in Organick, supra. Techniques for designing primers are known to those of skill in the art and tools exist to automate primer design. See Ye et al. *Primer-Blast: A tool to design target-specific primers for polymerase chain reaction* BMC Bioinformatics vol. 13 article 134 (2012).

Standard primers such as those described in the references above are referred to in this disclosure as "unique primers." Unique primers have specific sequences that vary along their length. Unique primers may include short homopolymer sequences (e.g., two or three nucleotides). However, in some implementations unique primers may exclude homopolymer sequences of any length. Every nucleotide in a unique primer contributes to increasing the address space. Even a single, relatively short unique primer can provide an address space with hundreds of thousands of unique addresses.

Another type of primer is the homopolymer primer. Homopolymer primers are primers that have the same nucleotide along their entire length. Examples of homopolymer primers are AAAA, TTTT or UUUU, GGGG, and CCCC. Although shown as four-nucleotide long primers in this example, homopolymer primers may be longer. Homopolymer primers may be the same length as the paired unique primer. Homopolymer primers may also be longer than the paired unique primer. In a pool of polynucleotides that each includes one homopolymer primer binding site, there are at most four options for the homopolymer primer using standard nucleotides. Thus, the homopolymer primer can provide an address space of four. If variation in homopolymer primer binding sites are used to create additional address space, homopolymer primers can quadruple the address space provided by the unique primer.

Template Independent Polymerases

Template independent polymerases are DNA or RNA polymerases that perform de novo oligonucleotide synthesis without use of a template strand. Currently known template independent polymerases include TdT, poly(A) polymerase, and tRNA nucleotidyltransferase. TdT includes both the full-length wild-type enzyme, as well as modified enzymes that are truncated or internally modified. One example of modified TdT is provided in U.S. Pat. No. 10,059,929. An example of truncated TdT is provided in U.S. Pat. No. 7,494,797. Thus, template independent polymerase as used herein includes full-length wild-type, truncated, or otherwise modified TdT, poly(A) polymerase, tRNA nucleotidyltransferase, and any other polymerases that can perform template independent synthesis of polynucleotides. Template independent polymerase as used herein does not encompass modifications of TdT, poly(A) polymerase, or tRNA nucleotidyltransferase that render those enzymes incapable of performing template independent nucleotide polymerization.

TdT evolved to rapidly catalyze the linkage of naturally occurring deoxynucleotide triphosphates (dNTPs). TdT adds nucleotides indiscriminately to the 3' hydroxyl group at the 3' end of single-stranded DNA. TdT performs unregulated synthesis adding any available dNTP. TdT uses an existing single-stranded polynucleotide referred to as an "initiator" as the starting point for synthesis. Initiators as short as three nucleotides have been successfully used with TdT for enzymatic synthesis of DNA. Suitable initiator length ranges from three nucleotides to about 30 nucleotides or longer. During the polymerization, the template independent polymerase holds a single-stranded DNA strand (which initially is only the initiator) and adds dNTPs in a 5'-3' direction. TdT activity is maximized at approximately 37° C. and performs enzymatic reactions in an aqueous environment.

However, using TdT to create a polynucleotide with a pre-specified arbitrary sequence requires regulation and control of the TdT activity. One technique to regulate TdT activity is limiting the available nucleotides to only a single species of dNTP or NTP. Thus, providing only one choice forces the enzyme to add that type of nucleotide. However, this does not prevent the TdT from adding that nucleotide multiple times thereby creating homopolymers. Techniques for limiting homopolymer creation by TdT include using nucleotides with removable protecting groups, covalently coupling individual nucleotides to TdT enzymes, and limiting the available quantity of nucleotides. Examples of these techniques are briefly described below.

One technique for controlling enzymatic synthesis of oligonucleotides with TdT uses a modified TDT enzyme and dNTP analogs with protecting groups to prevent unregulated nucleotide addition. An example of this technique is described in U.S. Pat. No. 10,059,929. Techniques for enzymatic polynucleotide synthesis that use protecting groups typically flood a reaction tube with only one species of dNTP. The protecting group prevents polymerization so only a single nucleotide is added to the growing polynucleotide strand. Once coupling has taken place, the free dNTPs are washed away, the protecting group is removed with a deblocking solution, and the system is primed for the next round of single-nucleotide addition.

Another technique for enzymatic synthesis uses TdT enzymes each tethered to a single dNTP by a cleavable linker. See Sebastian Palluck et al., De novo *DNA synthesis using polymerase-nucleotide conjugates,* 36(7) Nature Biotechnology 645 (2018) and WO 2017/223517. In this system, the TdT acts as its own protecting group preventing further chain elongation.

A third technique for nucleotide synthesis using TdT regulates activity of the polymerase by including the enzyme apyrase, which degrades nucleoside triphosphates into their TdT-inactive diphosphate and monophosphate precursors. See Henry H. Lee et al., *Terminator-free template-independent Enzymatic DNA Synthesis for Digital Information Storage,* 10:2383 Nat. Comm. (2019) and WO 2017/17654. Apyrase limits polymerization by competing with TdT for nucleoside triphosphates.

Although synthesis of specific, varied sequences requires tight control over the activity of a template independent polymerase, it relatively easy to create homopolymers. Because template independent polymerases such as TdT perform unregulated synthesis, they can easily create homopolymers if provided with only a single species of dNTP or NTP (e.g., only dATP, dCTP, dGTP, dTTP, or UTP).

As long as reaction conditions are suitable and free nucleotides remain, TdT will continue adding the nucleotide creating a homopolymer. The nucleotides used for unregulated synthesis do not include blocking groups which would prevent the creation of homopolymers. Homopolymer length may be controlled by regulating the reaction time. However, there may be variation in the length of homopolymer sequences even in a population of homopolymers created under the same conditions. Thus, in some implementations the length of a homopolymer primer binding site is not predetermined.

Solid-phase synthesis techniques may be used for enzymatic synthesis of polynucleotides. Solid-phase synthesis is a method in which molecules are covalently bound on a solid support material and synthesized step-by-step in a single reaction vessel. Solid-phase synthesis may be performed on solid support that is an integrated circuit (IC) or "chip." Solid phase synthesis may be used to make many types of polymers including, but not limited to, polynucleotides.

Solid-phase synthesis may be performed on a microelectrode array. Array-based synthesis provides addressability and site-specific adaptation of reaction environments by using a rigid or semi-rigid surface that is substantially flat as the solid substrate for polynucleotide synthesis. This design provides multiple separately adjustable reaction environments with a structure that is more compact and requires less physical manipulation than a comparable system using beads and test tubes. Changes of electrical current in the microelectrode array can control reaction conditions that permit or prevent the activity of template independent polymerases in the proximity of a given electrode. Spatial control may be implemented by removing protecting groups attached to nucleotides only at a selected location on the array or by other techniques such as location-specific regulation of enzymatic activity. Techniques for solid-phase synthesis using template independent polymerases are discussed in U.S. patent Ser. No. 16/563,797 entitled "Array-Based Enzymatic Oligonucleotide Synthesis" filed on Sep. 9, 2019.

Polynucleotide Sequencing

A sequencing technology that can be used is sequencing-by-synthesis (Illumina® sequencing). Sequencing by synthesis is based on amplification of DNA on a solid surface using fold-back PCR and anchored primers. The DNA is fragmented, and adapters are added to the 5'- and 3'-ends of the fragments. DNA fragments that are attached to the surface of flow cell channels are extended and bridge amplified. The fragments become double-stranded, and the double-stranded molecules are denatured. Multiple cycles of solid-phase amplification followed by denaturation can create several million clusters of approximately 1,000 copies of single-stranded DNA molecules of the same template in each channel of a flow cell. Primers, DNA polymerase, and four fluorophore-labeled, reversibly terminating nucleotides are used to perform sequential sequencing. After nucleotide incorporation, a laser is used to excite the fluorophores, an image is captured, and the identity of the first base is recorded. The 3' terminators and fluorophores from each incorporated base are removed and the incorporation, detection, and identification steps are repeated. Sequencing-by-synthesis has a relatively low error rate (e.g., less than 1%) and produces read lengths of a few hundred base pairs. This length is generally sufficient to read the entire length of a single synthetic polynucleotide.

Another sequencing technique that can be used is nanopore sequencing. A nanopore is a small hole of the order of one nanometer in diameter. Immersion of a nanopore in a conducting fluid and application of a potential across the nanopore results in a slight electrical current due to conduction of ions through the nanopore. The amount of current that flows through the nanopore is sensitive to the size of the nanopore. As a polynucleotide molecule passes through a nanopore, each nucleotide on the polynucleotide molecule obstructs the nanopore to a different degree depending on the base. Thus, the change in the current passing through the nanopore as the polynucleotide molecule passes through the nanopore represents a reading of the polynucleotide. Nanopore sequencing has much higher error rates (e.g., over 10%) than sequencing-by-synthesis. However, the read lengths of Nanopore sequencing are much longer—up to 800,000 bp long.

FIG. 1 is a schematic diagram of a process 100 process that uses random access to selectively retrieve polynucleotides from a polynucleotide data storage system. The process 100 may be performed with a homopolymer primer and a unique primer as described above.

At operation 102, the process 100 can include obtaining digital data 104. The digital data 104 can include a sequence of bits (e.g., 1s and 0s) that can be processed by a computing device. In illustrative implementations, the digital data 104 can be related to at least one of audio content, video content, image content, or text content. The digital data 104 can be associated with one or more data files, software applications, or the like.

At operation 106, the process 100 can include encoding the digital data 104 as one or more polynucleotide sequences 108. The polynucleotide sequence 108 may be represented as a string of letters, an alphabetical representation, stored electronically in the memory of a computing device. The encoding of the digital data 104 as polynucleotide sequences 108 can be performed according to one or more techniques that associate one or more bits of the digital data 104 with one or more nucleotides. The polynucleotide sequences 108 encoding digital data 104 may be referred to as payload sequences. Techniques to encode digital data 104 in polynucleotides are described in U.S. Pat. App. Publication No. 2017/0141793 entitled "Error Correction For Nucleotide Data Stores" filed on Jan. 22, 2016, U.S. Pat. App. Publication No. 2018/0223341 entitled "Primer Design For Retrieval Of Stored Polynucleotides" filed on Feb. 8, 2017, U.S. Pat. App. Publication No. 2018/0265921 entitled "Random Access Of Data Encoded By Polynucleotides" filed on Mar. 15, 2017, and U.S. Pat. App. Publication No. 2018/0211001 entitled "Trace Reconstruction From Noisy Polynucleotide Sequencer Reads" filed on Jun. 14, 2017, and Organick, supra.

In an example encoding, a first group of bits can be associated with a first nucleotide, a second group of bits with a second nucleotide, a third group of bits with a third nucleotide, and a fourth group of bits with a fourth nucleotide. For example, a first bit pair 00 can correspond to a first nucleotide, such as A; a second bit pair 01 can correspond to a second nucleotide, such as C; a third bit pair 10 can correspond to a third nucleotide, such as G; and a fourth bit pair 11 can correspond to a fourth nucleotide, such as T. In another illustrative example, the digital data 104 can be mapped to a base-4 string with each number in base-4 mapping to a corresponding letter representing a nucleotide. To illustrate, 0, 1, 2, and 3 can each map to one of A, C, G, or T. In an additional illustrative example, the digital data 104 can be mapped to a base-3 string with a nucleotide mapping to each number of the base 3 string (e.g., 0, 1, 2) based on a rotating (or rolling) code.

At operation 110, the process 100 includes enzymatically synthesizing polynucleotides 112 and adding the polynucleotides 112 to a container 114 of a polynucleotide data storage system that holds a pool of polynucleotides 116. The polynucleotides 112 include nucleotides corresponding to the polynucleotide sequences 108 generated at operation 106. The polynucleotides 112 also include additional nucleotide sequences that do not encode digital data 104 such as primer binding sites.

The design of the sequences for the polynucleotides 112 may create groups of polynucleotides 112 that share a logical relationship and that have the same primer binding sites. One example of a logical relationship is encoding digital data 104 from the same data file. The container 114 may be any type of physically isolated volume such as a well, tube, chamber, droplet, etc. The container 114 may contain an undifferentiated mixture of polynucleotides 112 encoding many different sets of digital data 104 such as many different data files. Although only a single container 114 is shown, a polynucleotide data storage system may include any number of separate containers. Storage in separate containers provides physical addressing that can be used to retrieve one group of polynucleotides instead of another even if there are no molecular characteristics to distinguish the two groups of polynucleotides.

Enzymatic synthesis may be performed by any template independent polymerase such as TdT. Enzymatic synthesis is performed under reaction conditions suitable for the specific enzyme and synthesis technique. Enzymatic synthesis may be performed in the container 114 or at a different location followed by transfer of the polynucleotides 112 to the container 114. Enzymatic synthesis is used because it can readily create homopolymer sequences that function as homopolymer primer binding sites.

At operation 118, random access of specific polynucleotides from the pool of polynucleotides 116 is performed by PCR. To improve stability of the molecules, the polynucleotides 112 in the pool 116 may be stored as double-stranded molecules 120. In response to a request for specific digital data encoded by one or more of the polynucleotide 112, a first primer 122 and a second primer 124 that correspond to primer target sites on the one or more polynucleotides 112 can be identified and obtained. The primers 122, 124 may be identified, for example, by the use of a data structure (e.g., look-up table, database, key, or the like) stored in the memory of a computing device. In an implementation, the data structure may include lists of primers and the corresponding digital data 104 such as file names.

The primers 122, 124 may be synthesized on demand or synthesized in advance and stored until needed. The primers 122, 124 may be synthesized by any technique for creating polynucleotides such as phosphoramidite synthesis or enzymatic synthesis. Homopolymer primers may be created by enzymatic synthesis because phosphoramidite synthesis is inefficient at creating homopolymers of A, G, or C longer than about 10 nucleotides.

In one implementation, desalted, unpurified primers may be obtained from a commercial source such as Integrated DNA Technologies of Coralville, Iowa. The primers may then be resuspended to 100 uM in 1× TE buffer (pH 7.5). The primers 122, 124 are then used to selectively amplify at least a portion of the pool 116 that contains the one or more polynucleotides 112. As described above, the amplification is specific for the polynucleotides encoding the specific digital data and does not amplify polynucleotides that encode different digital data.

At operation 126, the specific polynucleotides created by PCR amplification of the pool of polynucleotides 116 are sequenced. An amplification product 128 is created by PCR amplification of the pool of polynucleotides 116. Amplification products are many copies of the same double-stranded polynucleotide. Sequencing may be performed by a polynucleotide sequencer 130 that generates sequence data 132. Sequence data 132 may be referred to as "reads." A read can represent a determination of which of the four nucleotides—A, G, C, and T (or U)—in a strand of DNA (or RNA) is present at a given position in the sequence. The format of reads varies based on the specific device used to generate the sequence data 132. One format for reads is the FASTQ format.

Any known or future developed technique for sequencing polynucleotides may be used. Due to the selective amplification performed at operation 118 with the primers 122 and 124, the sequence data 132 will contain the payload sequences of the one or more polynucleotides 112 that encode the specific digital data.

At operation 134, the sequence data 132 is decoded to retrieve digital data 136. The digital data 136 should be the same as the digital data 104 that was originally encoded. A variety of techniques for error correction in polynucleotide data storage systems are known to those of skill in the art. Techniques to decode and reconstruct digital data 104 encoded in polynucleotides are described in U.S. Pat. App. Publication No. 2017/0141793 entitled "Error Correction For Nucleotide Data Stores" filed on Jan. 22, 2016, U.S. Pat. App. Publication No. 2018/0223341 entitled "Primer Design For Retrieval Of Stored Polynucleotides" filed on Feb. 8, 2017, U.S. Pat. App. Publication No. 2018/0265921 entitled "Random Access Of Data Encoded By Polynucleotides" filed on Mar. 15, 2017, and U.S. Pat. App. Publication No. 2018/0211001 entitled "Trace Reconstruction From Noisy Polynucleotide Sequencer Reads" filed on Jun. 14, 2017, and Organick, supra. Thus, in this disclosure, the digital data 104 provided to the polynucleotide data storage system and the digital data 136 obtained after decoding may be considered identical.

Figure 2:
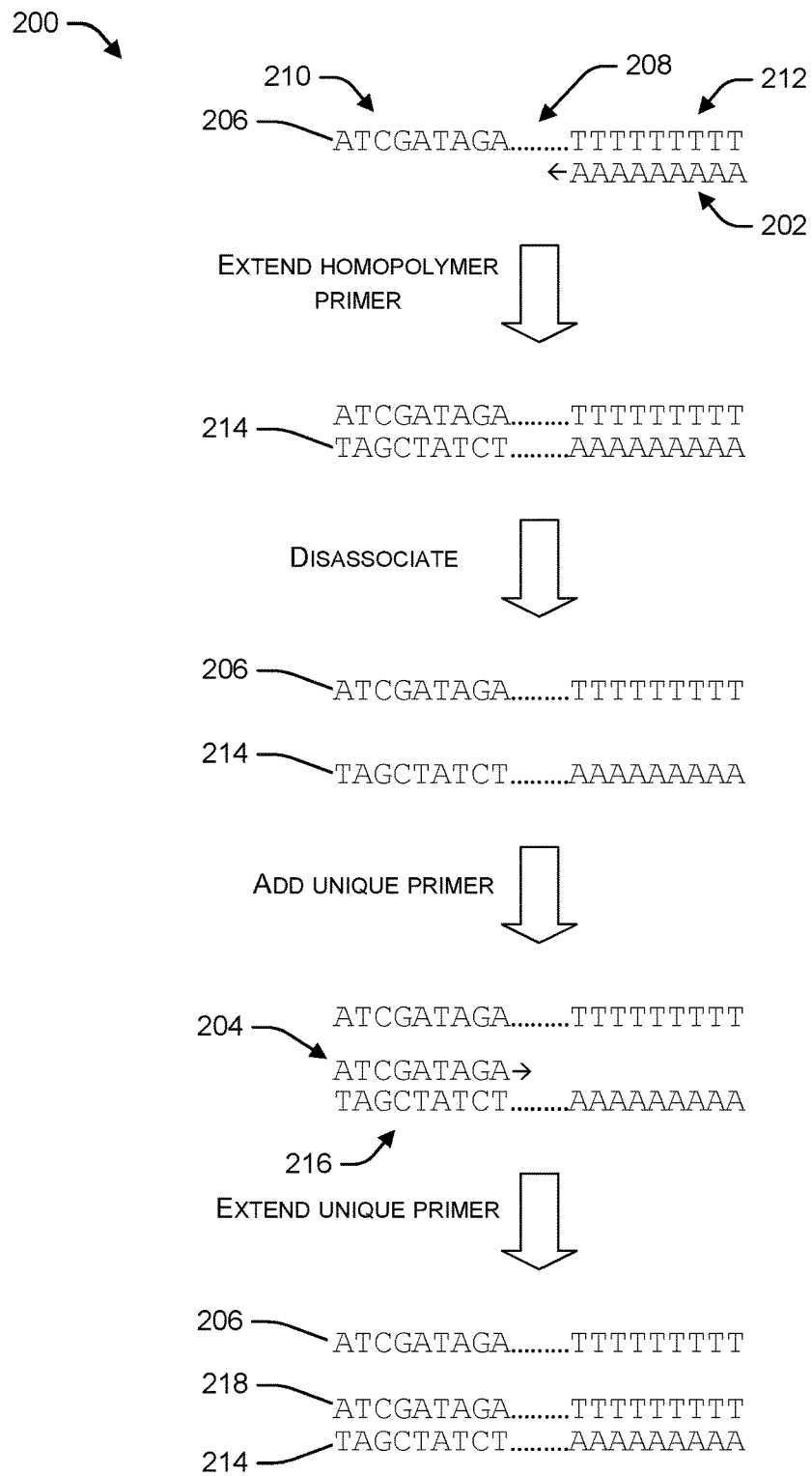
FIG. 2 shows a schematic representation of a PCR amplification technique that uses a homopolymer and a unique polymer to amplify a polynucleotide.

FIG. 2 shows a schematic diagram 200 of a PCR amplification technique that uses a homopolymer primer 202 and a unique primer 204 to amplify a polynucleotide 206. The polynucleotide 206 may be the same as the polynucleotide 112 of FIG. 1. The PCR may be performed using a PCR reaction mixture.

The polynucleotide 206 includes a payload region 208 between a unique primer binding site 210 and a homopolymer primer binding site 212. The payload region 208 may encode digital data. In some implementations, the payload region 208 may be about 100-200 nucleotides long. The payload region 208 is illustrated as a series of dots in FIG. 2. The polynucleotide 206 may exist as a single-stranded molecule or as a double-stranded molecule. If it is a double-stranded molecule, the polynucleotide 206 can disassociate into two single-stranded molecules during the PCR process.

The homopolymer primer 202 hybridizes to the homopolymer primer binding site 212. The homopolymer primer binding site 212 is a stretch of a single nucleotide that is complementary to the single nucleotide of the homopolymer primer 202. The length of a homopolymer primer binding site 212 may vary in a population of polynucleotides due to the variations in the numbers of nucleotides added by uncontrolled synthesis. If, for example, the homopolymer primer 202 is formed from the nucleotide adenine (A) then the homopolymer primer binding site 212 is a series of thiamine (T) nucleotides. The homopolymer primer 202 may the same length as the homopolymer primer binding site 212, longer, or shorter. The homopolymer primer 202 is illustrated in FIG. 2 with a length of nine nucleotides, but it may be shorter or longer.

The sequence of the homopolymer primer 202 and/or the homopolymer primer binding site 212 may include nucleotides that are not the same as the other nucleotides. For example, there may be other nucleotides included within a homopolymer sequence as the result of synthesis errors. However, any deviation from a constant homopolymer sequence is such that it does not prevent hybridization under suitable reaction conditions.

A template-dependent polymerase extends the homopolymer primer 202 by sequentially incorporating nucleotide triphosphates that are complementary to the polynucleotide 206. This creates a complementary polynucleotide 214. The template-dependent polymerase and the nucleotide triphosphates may be provided as part of a PCR reaction mixture.

Once formed, the complementary polynucleotide 214 is disassociated from the polynucleotide 206 during PCR by elevated temperatures. This creates two single-stranded polynucleotides 206, 214 that include complementary binding sites for unique primers and complementary homopolymer regions.

The unique primer 204 is added and hybridizes to the unique primer binding site 216 in the complementary polynucleotide 214. Because of the complementarity between primers and primer binding sites and between the two strands of a double-stranded polynucleotide, the sequence of the unique primer 204 that hybridizes to the complementary polynucleotide 214 may be the same as the unique primer binding site 210 of the polynucleotide 206. If the complementary polynucleotide 214 is present in a pool of polynucleotides that includes unique primer binding sites with different sequences which do not hybridize to the unique primer 204, those other polynucleotides will not be exponentially amplified during PCR.

Although the homopolymer primer 202 and the unique primer 204 are illustrated as being added sequentially in FIG. 2, in implementations both primers 202, 204 will be added at the same time before thermocycling begins. Additionally, although FIG. 2 illustrates the homopolymer primer 202 as being complementary to the polynucleotide 206 and the unique primer 204 as being complementary to the complementary polynucleotide 214 the relationship may be switched. In other words, the unique primer 204 may be complementary to a polynucleotide 206 that is originally present and the homopolymer primer 202 may be complementary to the complementary polynucleotide 214 generated by extension of the unique primer 204.

The unique primer 204 is extended by a template-dependent polymerase that sequentially incorporates nucleotides complementary to the complementary polynucleotide 214. This creates a new polynucleotide 218 with the same sequence as the original polynucleotide 202. This process is repeated multiple times exponentially amplifying the number of copies of the polynucleotide 206.

Figure 3:
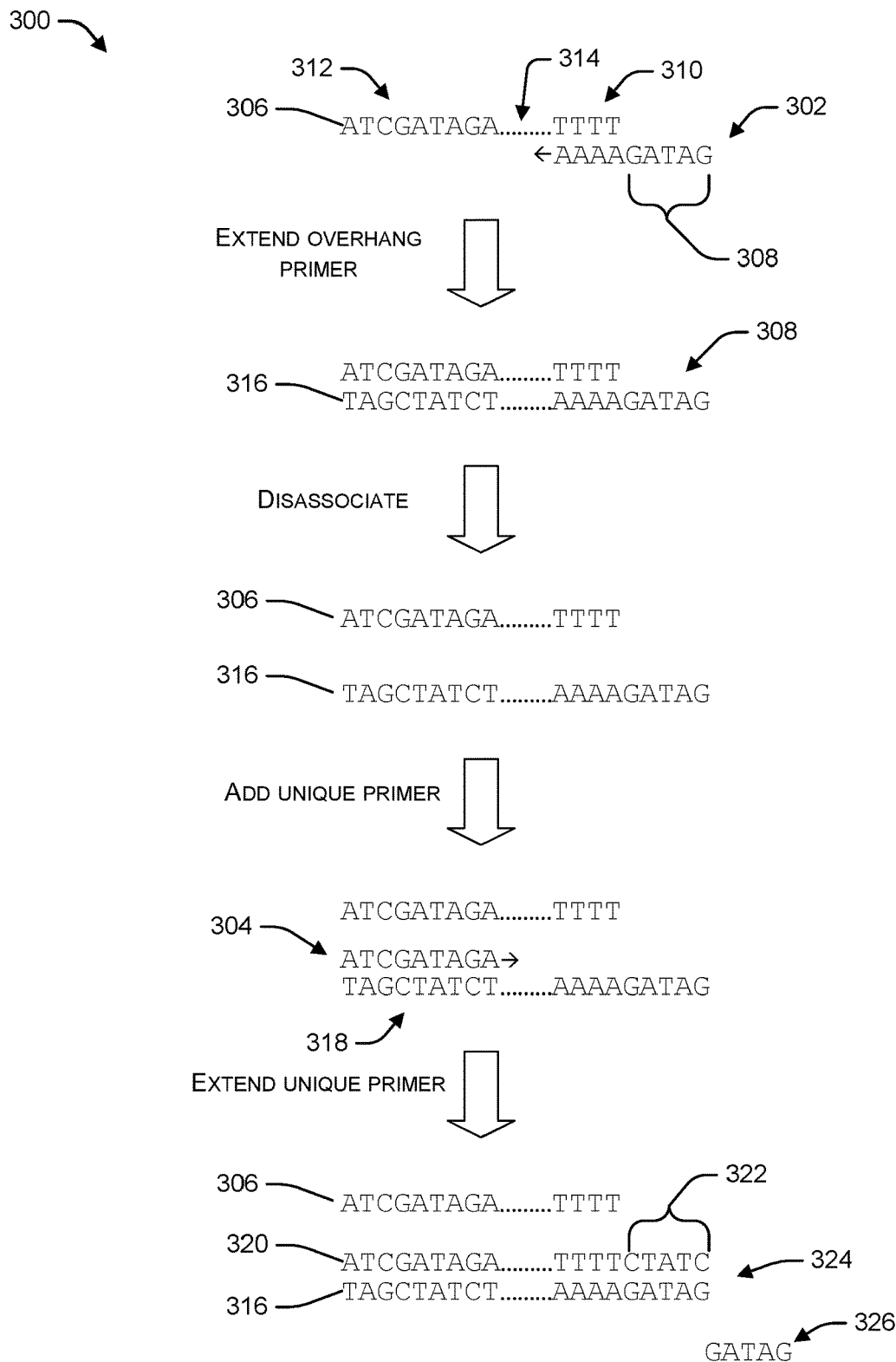
FIG. 3 shows a schematic representation of a PCR amplification technique that uses an overhang primer and a unique polymer to amplify a polynucleotide and to add a unique nucleotide sequence to the polynucleotide.

FIG. 3 shows a schematic representation 300 of a PCR amplification technique that uses an overhang primer 302 and a unique primer 304 to amplify a polynucleotide 306 and add a unique nucleotide sequence 308 to the polynucleotide 306. The unique nucleotide sequence 308 can provide additional address space beyond that available from the combination of the homopolymer primer binding site 310 and the unique primer binding site 312. Adding the unique nucleotide sequence 308 may also allow two different groups of nucleotides that otherwise share the same primer binding sites to be combined in a single pool while maintaining separate addresses for each.

The polynucleotide 306 includes a payload region 314 that may encode digital data, the unique primer binding site 312, and the homopolymer primer binding site 310. The overhang primer 302 is a primer that comprises a homopolymer region complementary to the homopolymer primer binding site 310 and a unique nucleotide sequence 308 that does not hybridize to the homopolymer primer binding site 310. The unique nucleotide sequence 308 overhangs the end of the polynucleotide 306 with the homopolymer primer binding site 310. The unique nucleotide sequence 308 is a sequence of varied nucleotides that is not a homopolymer but may contain short homopolymer sequences (e.g., two or three nucleotides long). In an implementation, the unique nucleotide sequence 308 may exclude homopolymers. In an implementation, any short homopolymer sequences in the unique nucleotide sequence 308 are homopolymers of a different nucleotide than the homopolymer region.

Extension of the overhang primer 302 by a template-dependent polymerase creates a complementary polynucleotide 316 that is complementary to the polynucleotide 306 and includes the unique nucleotide sequence 308. The polynucleotide 306 and the complementary polynucleotide 316 are disassociated and the unique primer 304 hybridizes to the unique primer binding site 318 of the complementary polynucleotide 316. Extension of the unique primer 304 creates a new polynucleotide 320 that is complementary to the complementary polynucleotide 316 and includes a complementary unique nucleotide sequence that may function as a second unique primer binding site 322.

This produces a new double-stranded polynucleotide 324 that no longer has a homopolymer sequence at one end but instead has unique nucleotides sequences on either side of the payload region 314. The first is the unique primer binding site 312 that was present originally in the polynucleotide 306. The second is the unique nucleotide sequence 308 added by the overhang primer 302. A second unique primer 326 that hybridizes to complementary unique nucleotide sequence 322 may be used together with the unique primer 304 to specifically amplify the new double-stranded polynucleotide 324. The second unique primer 326 may include only a sequence that hybridizes to the complementary unique nucleotide sequence 322. Alternatively, the second unique primer 326 may also include a homopolymer region (not shown) that hybridizes to at least a portion of the homopolymer primer binding site 310. Thus, in some implementations, the overhang primer 302 may be used as the second unique primer 326.

Although the overhang primer 302 and the unique primer 304 are illustrated as being added sequentially in FIG. 3, in implementations both primers 302, 304 will be added at the same time before thermocycling begins. Additionally, although FIG. 3 illustrates the unique primer 302 as being complementary to the polynucleotide 306 and the unique primer 304 as being complementary to the complementary polynucleotide 316 the relationship may be switched. In other words, the unique primer 304 may be complementary to a polynucleotide 306 that is originally present and the overhang primer 302 may be complementary to the complementary polynucleotide 316 generated by extension of the unique primer 304.

Figure 4:
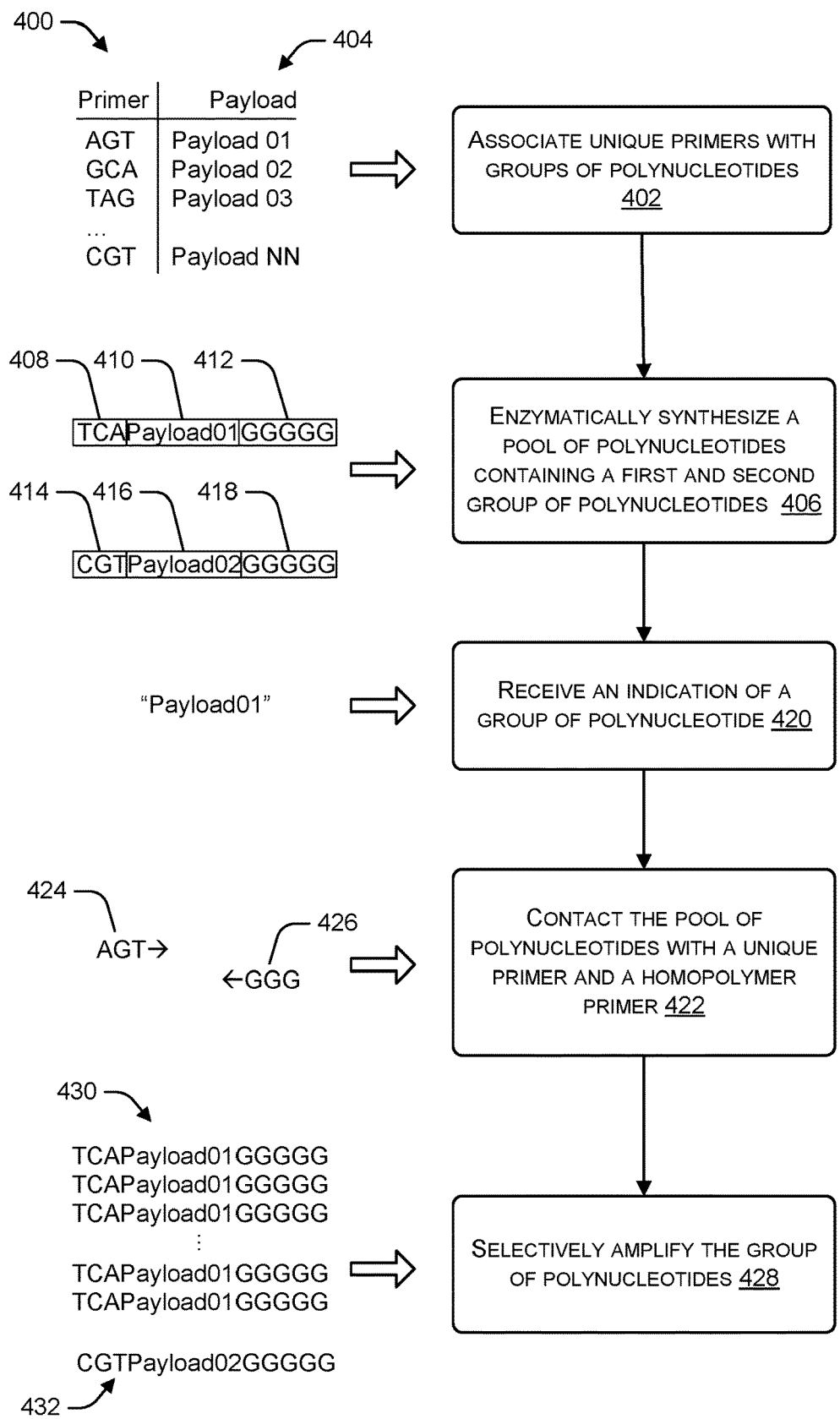
FIG. 4 is a schematic diagram of a process that uses a homopolymer primer and a unique primer to implement random access of a specific polynucleotide from a pool of polynucleotides.

FIG. 4 is a schematic diagram of a process 400 that uses a homopolymer primer and a unique primer to implement random access of a specific polynucleotide from the pool of polynucleotides. Portions of process 400 may be performed using the PCR amplification technique shown in FIG. 2.

At operation 402, unique primers are associated with groups of polynucleotides. Each group of polynucleotides includes a plurality of payload sequences that may be logically related or arbitrarily related to each other. One example of a logical relationship is encoding portions of the same data file. Each group of polynucleotides is associated with one of the unique primers. A group of polynucleotides may include many thousands or millions of different payload sequences. The correlation between unique primers and groups of polynucleotides may be recorded in a data structure 404 stored in memory of a computing device. The data structure 404 may be implemented as a look-up table, array, record, tree, linked list, or combinations thereof.

The unique primers may be associated with payloads during in silico design of polynucleotide sequences. Design of the sequences of the polynucleotides precedes synthesis. Design of a polynucleotide includes at least identification of the payload sequence, a unique primer binding site, a homopolymer primer binding site, and determination of the orientation of the primer binding sites relative to the payload sequence. Either primer binding site may be located at the 3'-end or the 5'-end of the payload sequence. The design of the polynucleotides may also include other sequences of nucleotides such as error correction regions, and regions that encode metadata. Various techniques for designing polynucleotide sequences to encode digital data are known to those of skill in the art.

At operation 406, a pool of polynucleotides is enzymatically synthesized. The pool of polynucleotides may be synthesized by providing the polynucleotide sequences designed at 402 to an automated or partially automated enzymatic synthesis system that performs synthesis with a template independent polymerase such as TdT to join nucleotides in specific sequences.

The pool of polynucleotides includes at least a first group of polynucleotides and a second group of polynucleotides. Although described with only two groups of polynucleotides, the pool may contain many thousands of different groups of polynucleotides. The first group of polynucleotides includes a first unique primer binding site 408, first payload regions 410 (e.g., payloads encoding digital data from a first data file), and a homopolymer primer binding site 412. The second group of polynucleotides includes a second unique primer binding site 414, second payload regions 416 (e.g., payloads encoding digital data from a second data file), and the same or different homopolymer primer binding site 418.

In an implementation, the homopolymer primer binding site 412 in the first group of polynucleotides and the homopolymer primer binding site 418 in the second group of polynucleotides may be the same homopolymer. Thus, in this implementation, the unique primer binding sites 408, 414 alone that differentiate the polynucleotides and provides addressability for random access. However, in an implementation, the homopolymer primer binding site 412 in the first group of polynucleotides is different than the homopolymer primer binding site 418 in the second group of polynucleotides. Different homopolymer primer binding sites can contribute to the address space. For example, use of four different homopolymer sequences in homopolymer primer binding sites within a pool of oligonucleotides can quadruple the address space provided by the unique primers.

The polynucleotides may be synthesized using controlled enzymatic synthesis for the unique primer binding sites 408, 414 and the payload regions 410, 416 to generate specific sequences of varied nucleotides. Controlled enzymatic synthesis typically proceeds by a series of nucleotide addition, washing, and unblocking/regulation steps. The desired nucleotide is added, and the template independent polymerase joins it the 3'-prime end of the growing polynucleotide. Excess nucleotides and the template independent polymerase are washed away. Unblocking removes a blocking group that prevents addition of more than one nucleotide. Regulation controls activity of the template independent polymerase and servers to limit addition of nucleotides. Regulation denies the polymerase something necessary to continue polymerization. In an implementation, nucleotides may be enzymatically degraded removing the substrates for the template independent polymerase. The template independent polymerase may also be regulated by controlling access to metal cofactors. Examples of techniques for regulating the activity of template independent polymerases are discussed in U.S. patent application Ser. No. 16/543,433 entitled "Regulation of Polymerase Using Cofactor Oxidation States" filed on Aug. 16, 2019, and U.S. patent application Ser. No. 16/563,797 entitled "Array-Based Enzymatic Oligonucleotide Synthesis" filed on Sep. 6, 2019.

Unregulated enzymatic synthesis may be used to synthesize the homopolymer primer binding sites 412, 418. Unregulated enzymatic synthesis takes advantage of template independent polymerases' ability to continually add nucleotides. A single species of nucleotide is provided without a blocking group. The template independent polymerase repeatedly adds that nucleotide creating a homopolymer. The reaction can be stopped by washing away the nucleotides and the template independent polymerase or by regulating activity of the polymerase using techniques such as those described above. The length of a homopolymer created by unregulated enzymatic synthesis may be difficult to control precisely leading to variations in the length of the homopolymer primer bindings sites 412, 418 among polynucleotides in the same group.

It is much more efficient to create a homopolymer primer binding site using unregulated enzymatic synthesis than it is to create a unique primer binding site using controlled enzymatic synthesis. To create a homopolymer primer binding site of any length involves only a single cycle of contacting a growing polynucleotide with nucleotides and the template independent polymerase. The reaction is begun and once the homopolymer sequence reaches the desired length (e.g., 20 nucleotides) it is ended. However, to create a 20-nucleotide unique polymer sequence requires 20 cycles of nucleotide addition, washing, and deblocking/regulation. This a longer process (about 20 times longer). It also uses more reagents such as nucleotides because excess is washed away with each cycle. Thus, replacing a second unique primer binding site with a homopolymer primer binding site increases the efficiency, speed, and decreases the cost of synthesizing polynucleotides.

At operation 420, an indication of a group of polynucleotides is received. The indication may be received by a computing device. In an implementation, the computing device may include logic to generate and provide instructions to automated equipment such as a microfluidics device or laboratory robotics that causes the automated equipment to obtain a primer associated with the group of polynucleotides. The specific primer may be identified by the computing device, for example, through reference to the data structure 404. The indication of the group of polynucleotides may be an indication of a data file. The specified data file may be correlated with the group of polynucleotides by the data structure 404 or in another way.

At operation 422, at least a portion of the pool of polynucleotides is contacted with a unique primer 424, a homopolymer primer 426, and a PCR reaction mixture. A portion of the pool of polynucleotides may be removed from the pool and placed into a different container (e.g., a tube or chamber of a thermocycler). The unique primer 424, the homopolymer primer 426, and the PCR reaction mixture may be brought into contact with the pool manually or by operation of an automated system.

At operation 428, the group of polynucleotides indicated at 420 is selectively amplified by PCR. The selectivity is provided by the unique primer 424 and by the design of the pool of polynucleotides. By creating a pool of polynucleotides in which the unique primer 424 will hybridize only to polynucleotides in the selected group, PCR may be used to amplify only the selected group of polynucleotides. If multiple different homopolymer primer binding sites 412, 418 are used in the pool then the homopolymer primer 426 may also contribute to the selectivity. Selective amplification creates many copies of the selected group of polynucleotides 430 without increasing the number of copies of the other groups of polynucleotides 432.

Figure 5:
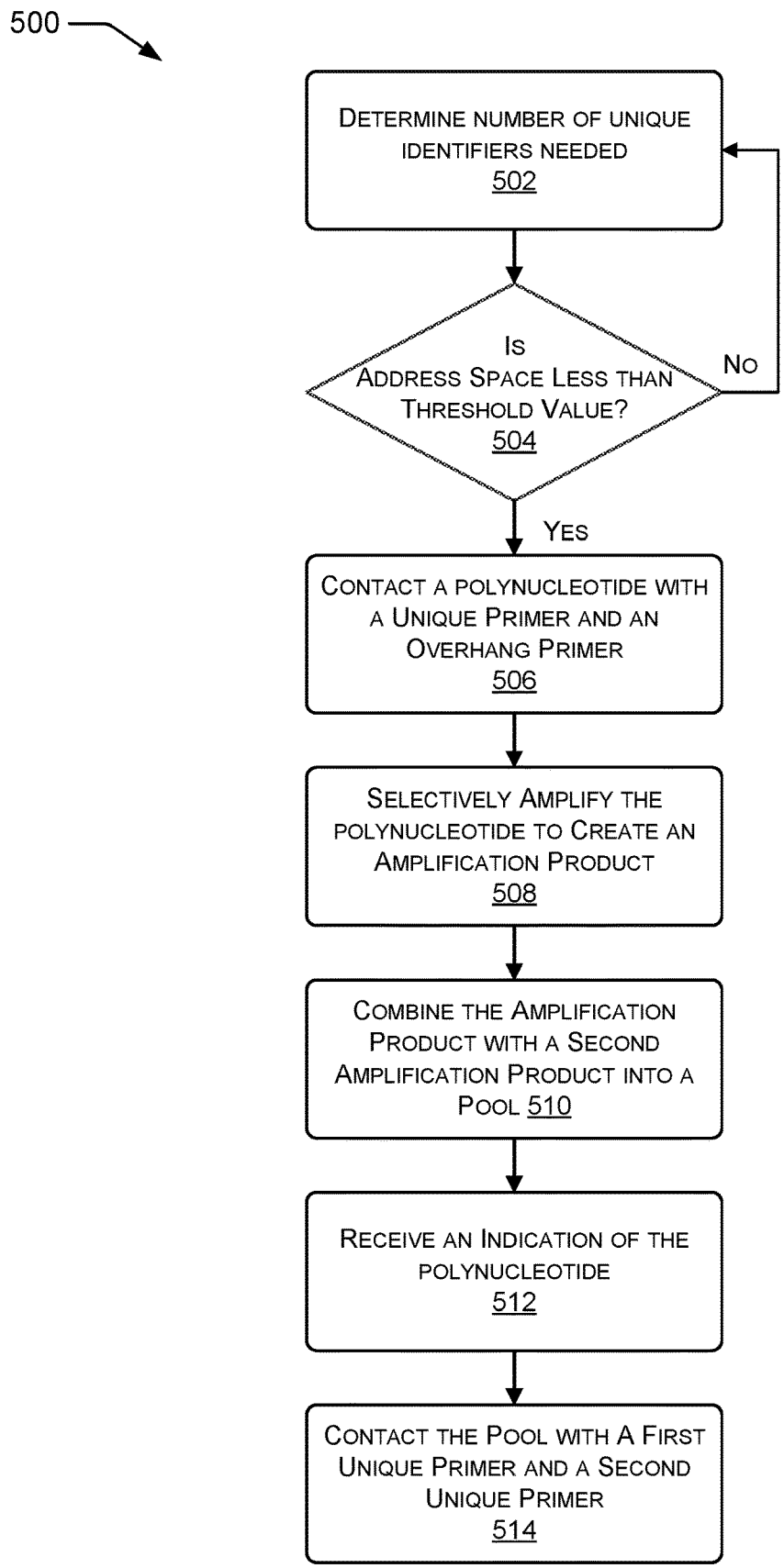
FIG. 5 is a schematic diagram of a process that adds a unique nucleotide sequence on to polynucleotides using overhang primers and combines two groups of polynucleotides into a single pool.

FIG. 5 is a schematic diagram of a process 500 that adds a unique nucleotide sequence onto polynucleotides by using overhang primers and combines two groups of polynucleotides into a single pool. Portions of process 500 may be performed using the PCR amplification technique shown in FIG. 3.

As discussed above, using a homopolymer primer together with a unique primer for random access reduces the available address space as compared using two unique primers. The address space limits the number of uniquely addressable groups of polynucleotides in a pool. If the address space needs to be increased, it would be desirable to do so without needing to resynthesize the entire pool with new primer binding sites.

There may also be a need to increase the address space if two groups of nucleotides that share the same unique primer binding site and the same homopolymer primer binding site are combined in a single pool. Without making a change to the polynucleotides, both groups would amplify together once combined making it impossible to selectively amplify one without the other. This problem can be addressed by adding different unique nucleotide sequences to each of the two groups of polynucleotides. The unique nucleotide sequences that are added can function as unique addresses for implementing random access.

At operation 502, a number of unique identifiers is determined. The unique identifiers are address locations in a pool of oligonucleotides that uniquely identify groups of polynucleotides. The unique identifiers may be implemented as primer binding sites. Polynucleotides that share the same primer binding sites, and thus are amplified by the same primers, belong to the same group of polynucleotides. The number of unique identifiers needed may be identified by determining how many different groups of polynucleotides will be combined in the same pool. If, for example, 10,000 different groups of polynucleotides are combined in a pool there will need to be 10,000 unique identifiers if each group is separately addressable.

At operation 504, it is determined if an available address space provides a number of unique identifiers that is less than a threshold value. The threshold value may be the number of unique identifiers determined at operation 502. In some implementations, the threshold value may be based on the number of unique identifiers but be less than the number of unique identifiers (e.g., 90% of the number of unique identifiers).

The address space determines the maximum number of unique identifiers and thus distinct groups that can be stored in a pool. The address space is affected by primer length and primer type. Longer primers provide a larger address space than shorter primers. Unique primers provide a larger address space than homopolymer primers.

If the available address space is less than the threshold value (i.e., there are too few unique identifiers) then process 500 proceeds along the "yes" path to operation 506. If the available address space is not less than the threshold value (i.e., there are enough unique identifiers) then process 500 proceeds along the "no" path and returns to operation 502. The number of unique identifiers needed may be continually evaluated or evaluated periodically as storage needs change.

At operation 506, a polynucleotide is contacted with a unique primer, an overhang primer, and a PCR reaction mixture. The polynucleotide includes a first unique primer binding site, a payload region, and a homopolymer primer binding site. The payload region may encode digital data. The unique primer hybridizes to the first unique primer binding site and includes a varied sequence of nucleotides that at least partially identifies the polynucleotide. The overhang primer includes a homopolymer region that hybridizes to the homopolymer primer binding site on the polynucleotide. The overhang primer also includes a unique nucleotide sequence that does not hybridize to the unique primer binding site or to the payload region of the polynucleotide. The polynucleotide may be contacted with the primers and PCR reaction mixture by placement into a reaction chamber of a thermocycler.

The polynucleotide is a polynucleotide that was enzymatically synthesized by a template independent polymerase. The unique primer binding site and the payload regions of the polynucleotide can be synthesized by controlled enzymatic synthesis. The homopolymer primer binding site in the polynucleotide can be synthesized by unregulated enzymatic synthesis in the presence of a single species of nucleotide.

At operation 508, the polynucleotide is selectively amplified by PCR to create an amplification product. Selective amplification uses the unique primer and the homopolymer primer to increase the number of copies of the polynucleotide without increasing the number of copies of other polynucleotides in the same pool. As shown in FIG. 3, amplification with the overhang primer generates an amplification product that includes the unique nucleotide sequence adjacent to the homopolymer sequence. The unique nucleotide sequence in the amplification product can function as a second unique primer binding site. Thus, subsequent amplification of polynucleotides from the amplification product can be performed using two unique primers (i.e., one that hybridizes to the first unique primer binding site and one that hybridizes to the second unique primer binding site created by the overhang primer).

At operation 510, the amplification product is combined with a second amplification product into a pool of polynucleotides. The second amplification product contains polynucleotides that share the same unique primer binding site but contain different payload regions. The payload regions of the second amplification product may, for example, encode digital data from a different data file. The polynucleotides in the second amplification product may also share the same homopolymer primer binding site. Thus, absent a modification the polynucleotides in the first and second amplification products would not be separately addressable if combined into the same pool.

That modification is provided to the polynucleotides in the first amplification product by amplification with the overhang primers at 508. A similar modification may be made to the polynucleotides in the second amplification product. For example, the second amplification product may be generated by PCR amplification using an overhang primer that includes a second unique nucleotide sequence different from the unique nucleotide sequence added to the first amplification product. The differences between the two unique nucleotide sequences may be such that they do not hybridize to each other and thus a primer that hybridizes to one will not hybridize to the other. The second unique nucleotide sequence added to the polynucleotides in the second amplification product may function as a third unique primer binding site distinct from the first unique primer binding site and from the second unique primer binding site.

At operation 512, an indication of one of the groups of polynucleotides in the pool created at operation 510 is received. The indication may be an indication of the polynucleotides of the first amplification product or the polynucleotides of the second amplification product. The indication may be received by a computing device. In an implementation, the computing device may include logic to generate and provide instructions to automated equipment such as a microfluidics device or laboratory robotics that causes the automated equipment to obtain primers associated with the group of polynucleotides. The indication may be interpreted by the computing device as specifying a set of primers. The specific primers may be identified by reference to a data structure stored in computer memory such as a look-up table.

For example, if the first amplification product is indicated, the corresponding primers are the first unique primer and the second unique primer. But if the second amplification product is indicated, the corresponding primers are the first unique primer and the third unique primer. Thus, it is the second and third primer binding sites (created by amplification with overhang primers) that allow for differentiation between polynucleotides in the first amplification product and the polynucleotides in the second application product.

At operation 514, the pool is contacted with the primers that correspond to the indication received at operation 512. This can be the first unique primer and one of the second unique primer or the third unique primer. If the indication at operation 512 indicates polynucleotides in the first amplification product, the primers will be the first unique primer and the second unique primer. If the indication at operation 512 indicates polynucleotides in the second amplification product, the primers will be the first unique primer and the third unique primer. The pool is also contacted with a PCR reaction mixture that may be the same or different than the PCR reaction mixture used at operation 506. PCR amplification will selectively amplify one but not both of the first amplification product and the second amplification product.

Figure 6:
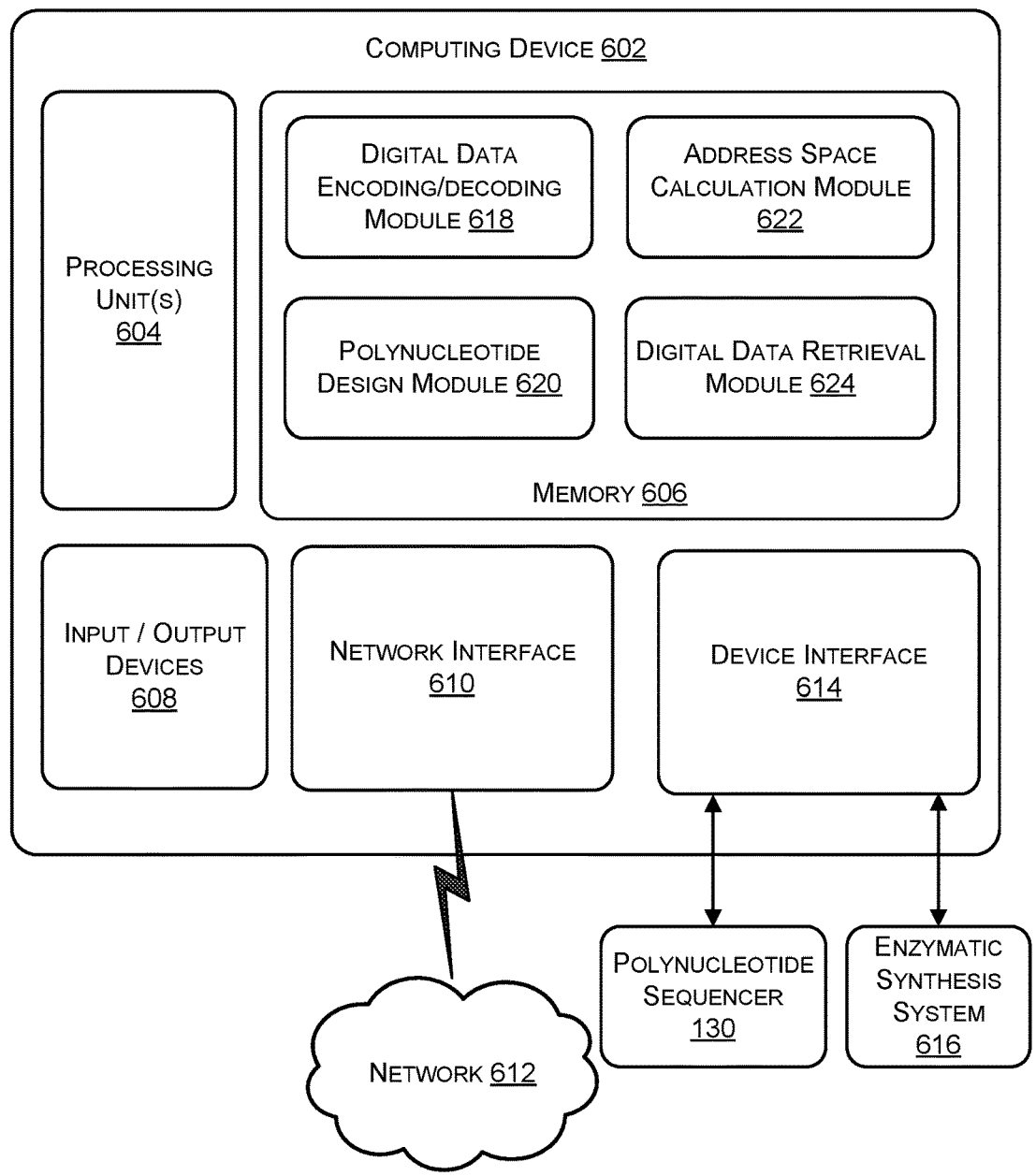
FIG. 6 shows a block diagram of an illustrative computing device to encode digital data in polynucleotides and to decode the digital data from polynucleotide sequences.

FIG. 6 shows a block diagram of an example system 600 including at least one computing device 602 that functions as a part of a polynucleotide data storage system. The computing device 602 can be implemented with one or more processing unit(s) 604 and memory 606, both of which can be distributed across one or more physical or logical locations. For example, in some implementations, the operations described as being performed by the computing device 602 can be performed by multiple computing devices. In some cases, the operations described as being performed by the computing device 602 can be performed in a cloud computing architecture.

The processing unit(s) 604 can include any combination of central processing units (CPUs), graphical processing units (GPUs), single core processors, multi-core processors, application-specific integrated circuits (ASICs), programmable circuits such as Field Programmable Gate Arrays (FPGA), and the like. In one implementation, one or more of the processing units(s) 604 can use Single Instruction Multiple Data (SIMD) parallel architecture. For example, the processing unit(s) 604 can include one or more GPUs that implement SIMD. One or more of the processing unit(s) 604 can be implemented as hardware devices. In some implementations, one or more of the processing unit(s) 604 can be implemented in software and/or firmware in addition to hardware implementations. Software or firmware implementations of the processing unit(s) 604 can include computer- or machine-executable instructions written in any suitable programming language to perform the various functions described. Software implementations of the processing unit(s) 604 may be stored in whole or part in the memory 606.

Alternatively, or additionally, the functionality of computing device 602 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Memory 606 of the computing device 602 can include removable storage, non-removable storage, local storage, and/or remote storage to provide storage of computer-readable instructions, data structures, program modules, and other data. The memory 606 can be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media can embody computer-readable instructions, data structures, program modules, or other data in a modulated data signal, such as a carrier wave, or other transmission mechanism. As defined herein, computer-readable storage media and communications media are mutually exclusive.

The computing device 602 can include and/or be coupled with one or more input/output devices 608 such as a keyboard, a pointing device, a touchscreen, a microphone, a camera, a display, a speaker, a printer, and the like. Input/output devices 608 that are physically remote from the processing unit(s) 604 and the memory 606 can also be included within the scope of the input/output devices 608.

Also, the computing device 602 can include a network interface 610. The network interface 610 can be a point of interconnection between the computing device 602 and one or more networks 612. The network interface 610 can be implemented in hardware, for example, as a network interface card (NIC), a network adapter, a LAN adapter or physical network interface. The network interface 610 can be implemented in software. The network interface 610 can be implemented as an expansion card or as part of a motherboard. The network interface 610 can implement electronic circuitry to communicate using a specific physical layer and data link layer standard, such as Ethernet or Wi-Fi. The network interface 610 can support wired and/or wireless communication. The network interface 610 can provide a base for a full network protocol stack, allowing communication among groups of computers on the same local area network (LAN) and large-scale network communications through routable protocols, such as Internet Protocol (IP). The one or more networks 612 can include any type of communications network, such as a local area network, a wide area network, a mesh network, an ad hoc network, a peer-to-peer network, the Internet, a telephone network, a wired network, a wireless network, combinations thereof, and the like.

A device interface 614 can be part of the computing device 602 that provides hardware to establish communicative connections to other devices, such as a polynucleotide sequencer 130, an enzymatic synthesis system 616 that uses a template independent polymerase to synthesize polynucleotides. The device interface 614 can also include software that supports the hardware. The device interface 614 can be implemented as a wired or wireless connection that does not cross a network. A wired connection may include one or more wires or cables physically connecting the computing device 602 to another device. The wired connection can be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like. Alternatively, the polynucleotide sequence 130, the enzymatic synthesis system 616, or other hardware may be connected to the computing device 602 over the network 612.

The computing device 602 can include multiple modules that may be implemented as instructions stored in the memory 606 for execution by processing unit(s) 604 and/or implemented, in whole or in part, by one or more hardware logic components or firmware. The memory 606 can be used to store any number of functional components that are executable by the one or more processing units 604. In many implementations, these functional components can comprise instructions or programs that are executable by the one or more processing units 604 and that, when executed, implement operational logic for performing the operations attributed to the computing device 602. Functional components of the computing device 602 can be executed on the one or more processing units 604 for implementing the various functions and features related to generating polynucleotide sequences for the storage and retrieval of digital data as described herein. The functional components can include a digital data encoding module 618, a polynucleotide design module 620, an address space calculation module 622, and a digital data retrieval module 624. One or more of the modules, 618, 620, 622, and 624, can be used to implement at least a portion of the processes shown in FIGS. 1, 4, and 5.

The digital data encoding module 618 can include computer-readable instructions that are executable by the processing unit(s) 604 to encode digital data as an alphabetic, or other, representation of a sequence of nucleotides. The digital data encoding module 618 can obtain digital data from one or more sources. In some cases, the digital data can be stored by the memory 606 and obtained from there. Also, the digital data can be stored by a data storage device coupled to, or otherwise accessible to, the computing device 602. The digital data can be related to image content, video content, text content, audio content, combinations thereof, and so forth. The digital data can include a bit string comprised of 1s and 0s. In some cases, the digital data can be included in a data file.

The digital data encoding module 618 can encode the 1s and 0s of the digital data as a sequence of nucleotides, such as A, T, G, C, or U. In particular implementations, each 1 or 0 of the digital data can be encoded as a particular nucleotide. In some cases, groups of 1s and groups of 0s of the digital data can be encoded as a particular nucleotide. In various implementations, the 1s and 0s of the digital data can be converted to a number in a number system other than base-2 before encoding. For example, the 1s and 0s of the digital data can be converted to a base-3 format or a base-4 format before encoding.

In illustrative implementations, the digital data encoding module 618 can encode the 1s and 0s of the digital data according to a binary encoding scheme. For example, the digital data encoding module 618 can encode the series of bits 00 as a first nucleotide (e.g., A), the series of bits 01 as a second nucleotide (e.g., T), the series of bits 10 as a third nucleotide (e.g., G), and the series of bits 11 as a fourth nucleotide (e.g., C).

In other illustrative implementations, the digital data encoding module 618 can encode the 1s and 0s of the digital data according to a ternary encoding scheme. For example, the digital data encoding module 618 can convert the 1s and 0s of the digital data to modified digital data comprising 0s, 1s, and 2s. Subsequently, the digital data encoding module 618 can encode the 0s, 1s, and 2s of the modified digital data as nucleotides. In some implementations, the data encoding module 618 can encode the 0s, 1s, and 2s of the modified digital data as nucleotides according to a preceding nucleotide in the sequence of nucleotides. To illustrate, a 0 preceded by G could be encoded as T, while a 0 preceded by A could be encoded as C.

In additional illustrative implementations, the digital data encoding module 618 can encode the 1s and 0s of the digital data according to a base-4 encoding scheme. In an example, the digital data encoding module 618 can convert the 1s and 0s of the digital data to modified digital data comprising 0s, 1s, 2s, and 3s. In these situations, when 6 nucleotides are used to encode the digital data, each species of nucleotide used to do the encoding can correspond with a respective base-4 number. Thus, in a particular illustrative example, 0 can correspond with A, 1 can correspond with T, 2 can correspond with G, and 3 can correspond with C.

In some cases, the length of the polynucleotide sequences encoding the digital data can be limited. For example, if the length of the sequence of nucleotides encoding the digital data is greater than a particular number of nucleotides, the polynucleotide can become unstable and/or otherwise lose its linear arrangement, such as by forming secondary structures. In illustrative implementations, the sequences of nucleotides used to encode digital data can have from 60 to 300 nucleotides, from 80 to 150 nucleotides, from 90 to 120 nucleotides, or from 100 to 140 nucleotides. In situations where multiple sequences are used to encode the digital data, the digital data encoding module 618 can divide the bits of the digital data into segments. The digital data encoding module 618 can encode each of the segments of the digital data as a separate sequence of nucleotides. In some cases, the segments can be the same length, while in other situations, the segments can have varying lengths. In implementations where the segments have different lengths, the length of the segments can be within a range of lengths. The range of lengths can be based at least partly on a probability that polynucleotides may lose a linear structure when the length is greater than an upper threshold length or when the length is less than a lower threshold length.

The polynucleotide design module 620 can include computer-readable instructions that, when executed by the processing unit(s) 604, generate polynucleotide sequences that include payload regions which encode digital data as well as other regions that do not encode digital data. The polynucleotide design module 620 can use data corresponding to payloads produced by the digital data encoding module 618 to generate the polynucleotide data. The polynucleotide design module 620 can also utilize data corresponding to group identifiers associated with the payloads to generate polynucleotide data. Additionally, the polynucleotide design module 620 can design both unique primers and homopolymer primers to associate with the payloads to generate polynucleotide data. The polynucleotide design module 620 can design primers according to any currently known or later-developed techniques for PCR primer design.

In situations where a string of bits is divided into a number of segments before being encoded as multiple different payloads, addressing information can be assigned to each payload. The addressing information can indicate the segment of the bit string that is encoded and the location of the segment within the original bit string. The polynucleotide design module 620 can generate one or more nucleotides that encode this addressing information and add those nucleotides to the polynucleotide sequence. The polynucleotide design module 620 can also add nucleotides that correspond to error correction information. Further, the polynucleotide design module 620 can add nucleotides that correspond to a file identifier which may be distinct from the primer binding sites.

The polynucleotide design module 620 may determine identifiers for each group of polynucleotides. In some instances, the group identifies the data file that is encoded by the polynucleotides in the group. For example, the polynucleotide design module 620 can assign one or more group identifiers to respective groups that include the polynucleotides which encode digital data of a particular data file. The polynucleotide design module 620 can also generate metadata that indicates the group identifiers that correspond to the data file. The group identifiers may be primer binding sites that allow for selective amplification of polynucleotides belonging to the same group. The polynucleotide design module 620 can also pair homopolymer sequences with unique primer binding sites.

The polynucleotide sequences generated by the polynucleotide design module 620 can be used as instructions to synthesize polynucleotides. In some implementations, the polynucleotide design module 620 can communicate polynucleotide data corresponding to the polynucleotide sequences to one or more devices such as an enzymatic synthesis system 616. The polynucleotide design module 620 may also provide primer sequences to an oligonucleotide synthesizer that uses phosphoramidite chemistry or other non-enzymatic techniques to create polynucleotides.

The address space calculation module 622 can include computer-readable instructions that when executed by the processing unit(s) 604 determine an available or a necessary address space. The address space calculation module 622 can determine the address space needed to store groups of polynucleotides in the same pool. It may do this simply by counting the number of different groups of polynucleotides. The number of groups and the number of polynucleotides in each group determines the resolution of random access.

The address space calculation module 622 may also determine the available address space based on a set of unique primers and homopolymer primers. In an implementation, the address space may be determined by counting the number of different unique primers that satisfy all other existing constraints on primer design. In an implementation, the address space may be determined by multiplying the number of different unique primers (that satisfy all other constraints) by the number of homopolymer primer variations used in the pool. For example, if two different homopolymer sequences are used as homopolymer primer binding sites, this will double the address space.

The digital data retrieval module 624 can include computer-readable instructions that when executed by the processing unit(s) 604 can provide digital data in response to a request for the digital data. In some implementations, the digital data retrieval module 624 can receive a request to obtain digital data. For example, the digital data retrieval module 624 can receive a request for a data file including a digital image. The digital data retrieval module 624 can identify one or more primers and/or at least one file identifier that corresponds to the requested data. To illustrate, the digital data retrieval module 624 can parse a data structure, such as a lookup table, to identify the primers that correspond to the requested digital data.

The digital data retrieval module 624 can communicate with one or more devices, such as via the device interface 614, to request the polynucleotides that correspond to the group identifiers. In some implementations, the one or more devices in communication with the digital data retrieval module 624 can be coupled to, or otherwise associated with, a polynucleotide data storage system. In various implementations, the digital data retrieval module 624 can provide to another computing device the primers to be used to amplify the polynucleotides of the groups. Also, the digital data retrieval module 624 can access metadata indicating a storage location (e.g., one or more container identifiers) within a polynucleotide data storage system that stores polynucleotides which correspond to the requested digital data.

In particular implementations, the storage location can be identified based at least partly on matching the group identifiers associated with the requested digital data with the group identifiers associated with the containers of the polynucleotide data storage system. In some implementations, the digital data retrieval module 624 can provide the information regarding the primers and/or the storage location to one or more additional computing devices, such as a computing device coupled with a polynucleotide data storage system.

The digital data retrieval module 624 can receive the sequences of the polynucleotides from one or more devices, such as polynucleotide sequencer 130, and decode the polynucleotides using a reverse process from the encoding performed by the digital data encoding module 618. For example, in implementations where 00 in a string of bits is encoded as A, the digital data retrieval module 624 can decode each A in the polynucleotide sequences as 00. The digital data retrieval module 624 can reproduce the bit string of the digital data being requested and provide the bit string to one or more devices that requested the digital data. The digital data retrieval module 624 may also implement one or more error correction techniques in the decoding of polynucleotide sequences.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of storing and retrieving digital data in polynucleotides: encoding digital data in a payload sequence; associating the payload sequence with a unique primer; enzymatically synthesizing a polynucleotide having a sequence that includes a unique primer binding site that hybridizes with the unique primer, the payload sequence, and a homopolymer primer binding site; contacting the polynucleotide with the unique primer, a homopolymer primer that hybridizes to the homopolymer primer binding site, and a polymerase chain reaction (PCR) reaction mixture; selectively amplifying, by PCR, the polynucleotide; sequencing the polynucleotide to generate sequence data; and decoding the sequence data to retrieve the digital data.

Clause 2. The method of clause 1, wherein enzymatically synthesizing the polynucleotide comprises regulating activity of a template independent polymerase during synthesis of the unique primer binding site and the payload sequence.

Clause 3. The method of any of clauses 1-2, wherein enzymatically synthesizing the polynucleotide comprises synthesizing the homopolymer primer binding site by unregulated synthesis with a template independent polymerase in the presence of only a single species of nucleotide without blocking groups.

Clause 4. The method of any of clauses 1-3, wherein enzymatically synthesizing the polynucleotide comprises solid-phase synthesis with an end of the polynucleotide that includes the unique primer binding site attached to a solid substrate.

Clause 5. The method of any of clauses 1-4, wherein a length of the homopolymer primer binding site is not predetermined.

Clause 6. The method of any of clauses 1-5, further comprising: mixing the polynucleotide into a pool of polynucleotides that contains a second polynucleotide comprising a second unique primer binding site, a second payload sequence, and the homopolymer primer binding site; and receiving an indication of the polynucleotide.

Clause 7. A method of performing random access to obtain specific polynucleotides from a pool of polynucleotides, the method comprising: enzymatically synthesizing a pool of polynucleotides containing: a first group of polynucleotides each comprising a first unique primer binding site and a homopolymer primer binding site, and a second group of polynucleotides each comprising a second unique primer binding site and a same or different homopolymer primer binding site; receiving an indication of the first group of polynucleotides; contacting at least a portion of the pool of polynucleotides with a first unique primer complementary to the first unique primer binding site, a homopolymer primer complementary to at least a portion of the homopolymer primer binding site, and a PCR reaction mixture; and selectively amplifying, by PCR, the first group of polynucleotides.

Clause 8. The method of clause 7, wherein the first group of polynucleotides comprise first payload regions encoding portions of a first data file and the second group of polynucleotides comprise second payload regions encoding portions of a second data file.

Clause 9. The method of clause 8, wherein the indication of the first group of polynucleotides comprises an indication of the first data file.

Clause 10. The method of any of clauses 7-9, wherein the enzymatically synthesizing comprises synthesis by a template independent polymerase.

Clause 11. The method of clause 10, wherein the enzymatically synthesizing the homopolymer primer binding site comprises combining the template independent polymerase and a single species of nucleotides without blocking groups to perform unregulated enzymatic synthesis of the homopolymer primer binding site.

Clause 12. The method of any of clauses 10-11, wherein the enzymatically synthesizing the first unique primer binding site and the second unique primer binding site comprises combining the template independent polymerase and an ordered sequence nucleotides with blocking groups to perform controlled enzymatic synthesis of specific sequences of the first unique primer binding site and of the second unique primer binding site.

Clause 13. The method of any of clauses 10-12, wherein the enzymatically synthesizing the first unique primer binding site in the first group of polynucleotides comprises providing a previously synthesized oligonucleotide with the sequence of the first unique primer binding site as an initiator to the template independent polymerase.

Clause 14. A method comprising: contacting a polynucleotide comprising a first unique primer binding site, a payload region, and a homopolymer primer binding site with: a unique primer having a sequence that hybridizes to the first unique primer binding site, an overhang primer that hybridizes to the homopolymer primer binding site and that includes a unique nucleotide sequence which overhangs an end of the polynucleotide, and a PCR reaction mixture; and selectively amplifying, by PCR, the polynucleotide to create a first amplification product having a second unique primer binding site formed from the unique nucleotide sequence of the overhang primer.

Clause 15. The method of clause 14, wherein the unique nucleotide sequence of the overhang primer is not complementary to the first unique primer binding site or to the payload region of the polynucleotide.

Clause 16. The method of any of clauses 14-15, further comprising determining that an address space created at least in part by the first unique primer binding site provides a number of unique identifiers that is less than a threshold value.

Clause 17. The method of any of clauses 14-16, further comprising combining, into a pool, the first amplification product with a second amplification product having the first unique primer binding site, a different payload region, and a third unique primer binding site.

Clause 18. The method of any of clauses 17, further comprising: receiving an indication of the polynucleotide;

contacting the pool with a first unique primer that hybridizes to the first unique primer binding site, a second unique primer that hybridizes to the second unique primer binding site, and the same or different PCR reaction mixture; and selectively amplifying, by PCR, polynucleotides of the first amplification product.

Clause 19. The method of clause 17, further comprising: contacting the pool with a first unique primer that hybridizes to the first unique primer binding site, a third unique primer that hybridizes to the third unique primer binding site, and the same or different PCR reaction mixture; and selectively amplifying, by PCR, polynucleotides of the second amplification product.

Clause 20. The method of any of clauses 14-19, further comprising enzymatically synthesizing the polynucleotide with a template independent polymerase by synthesizing the homopolymer primer binding site by unregulated synthesis in the presence of only a single species of nucleotide.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for their particular cited teachings as well as for all that they disclose.

The invention claimed is:

1. A method of storing and retrieving digital data in polynucleotides:
encoding digital data in a payload sequence;
associating the payload sequence with a unique primer;
enzymatically synthesizing a polynucleotide having a sequence that includes a unique primer binding site that hybridizes with the unique primer, the payload sequence, and a homopolymer primer binding site;
contacting the polynucleotide with the unique primer, a homopolymer primer that hybridizes to the homopolymer primer binding site, and a polymerase chain reaction (PCR) reaction mixture;
selectively amplifying, by PCR, the polynucleotide;
sequencing the polynucleotide to generate sequence data; and
decoding the sequence data to retrieve the digital data.

2. The method of claim 1, wherein enzymatically synthesizing the polynucleotide comprises regulating activity of a template independent polymerase during synthesis of the unique primer binding site and the payload sequence.

3. The method of claim 1, wherein enzymatically synthesizing the polynucleotide comprises synthesizing the homopolymer primer binding site by unregulated synthesis with a template independent polymerase in the presence of only a single species of nucleotide without blocking groups.

4. The method of claim 1, wherein enzymatically synthesizing the polynucleotide comprises solid-phase synthesis with an end of the polynucleotide that includes the unique primer binding site attached to a solid substrate.

5. The method of claim 1, wherein a length of the homopolymer primer binding site is not predetermined.

6. The method of claim 1, further comprising:
mixing the polynucleotide into a pool of polynucleotides that contains a second polynucleotide comprising a second unique primer binding site, a second payload sequence, and the homopolymer primer binding site; and
receiving an indication of the polynucleotide.

7. A method of performing random access to obtain specific polynucleotides from a pool of polynucleotides, the method comprising:
enzymatically synthesizing a pool of polynucleotides containing:
a first group of polynucleotides each comprising a first payload region encoding a portion of a first digital data file, a first unique primer binding site, and a homopolymer primer binding site, and
a second group of polynucleotides each comprising a second payload region encoding a portion of a second digital data file, a second unique primer binding site, and a same or different homopolymer primer binding site;
receiving an indication of the first group of polynucleotides;
contacting at least a portion of the pool of polynucleotides with a first unique primer complementary to the first unique primer binding site, a homopolymer primer complementary to at least a portion of the homopolymer primer binding site, and a PCR reaction mixture; and
selectively amplifying, by PCR, the first group of polynucleotides.

8. The method of claim 7, wherein the first group of polynucleotides comprise first payload regions encoding portions of a first data file and the second group of polynucleotides comprise second payload regions encoding portions of a second data file.

9. The method of claim 8, wherein the indication of the first group of polynucleotides comprises an indication of the first digital data file.

10. The method of claim 7, wherein the enzymatically synthesizing comprises synthesis by a template independent polymerase.

11. The method of claim 10, wherein the enzymatically synthesizing the homopolymer primer binding site comprises combining the template independent polymerase and a single species of nucleotides without blocking groups to perform unregulated enzymatic synthesis of the homopolymer primer binding site.

12. The method of claim 10, wherein the enzymatically synthesizing the first unique primer binding site and the second unique primer binding site comprises combining the template independent polymerase and an ordered sequence nucleotides with blocking groups to perform controlled enzymatic synthesis of specific sequences of the first unique primer binding site and of the second unique primer binding site.

13. The method of claim 10, wherein the enzymatically synthesizing the first unique primer binding site in the first group of polynucleotides comprises providing a previously synthesized oligonucleotide with the sequence of the first unique primer binding site as an initiator to the template independent polymerase.

14. A method comprising:
contacting a polynucleotide comprising a first unique primer binding site, a payload region, and a homopolymer primer binding site with:
a unique primer having a sequence that hybridizes to the first unique primer binding site,
an overhang primer that hybridizes to the homopolymer primer binding site and that includes a unique nucleotide sequence which overhangs an end of the polynucleotide, and
a PCR reaction mixture; and
selectively amplifying, by PCR, the polynucleotide to create a first amplification product having a second unique primer binding site formed from the unique nucleotide sequence of the overhang primer.

15. The method of claim 14, wherein the unique nucleotide sequence of the overhang primer is not complementary to the first unique primer binding site or to the payload region of the polynucleotide.

16. The method of claim 14, further comprising determining that an address space created at least in part by the first unique primer binding site provides a number of unique identifiers that is less than a threshold value.

17. The method of claim 14, further comprising combining, into a pool, the first amplification product with a second amplification product having the first unique primer binding site, a different payload region, and a third unique primer binding site.

18. The method of claim 17, further comprising:
receiving an indication of the polynucleotide;
contacting the pool with a first unique primer that hybridizes to the first unique primer binding site, a second unique primer that hybridizes to the second unique primer binding site, and the same or different PCR reaction mixture; and
selectively amplifying, by PCR, polynucleotides of the first amplification product.

19. The method of claim 17, further comprising:
contacting the pool with a first unique primer that hybridizes to the first unique primer binding site, a third unique primer that hybridizes to the third unique primer binding site, and the same or different PCR reaction mixture; and
selectively amplifying, by PCR, polynucleotides of the second amplification product.

20. The method of claim 14, further comprising enzymatically synthesizing the polynucleotide with a template independent polymerase by synthesizing the homopolymer primer binding site by unregulated synthesis in the presence of only a single species of nucleotide.

* * * * *